(12) United States Patent
Hagg et al.

(10) Patent No.: US 10,524,860 B2
(45) Date of Patent: Jan. 7, 2020

(54) NEUTRAL ELECTRODE DEVICE, ELECTROSURGICAL INSTRUMENT COMPRISING A CORRESPONDING NEUTRAL ELECTRODE DEVICE

(71) Applicant: ERBE ELEKTROMEDIZIN GMBH, Tuebingen (DE)

(72) Inventors: Martin Hagg, Wannweil (DE); Peter Selig, Hechingen (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 1570 days.

(21) Appl. No.: 14/310,751

(22) Filed: Jun. 20, 2014

(65) Prior Publication Data
US 2014/0336644 A1    Nov. 13, 2014

Related U.S. Application Data

(62) Division of application No. 13/062,755, filed as application No. PCT/EP2009/006186 on Aug. 26, 2009, now abandoned.

(30) Foreign Application Priority Data

Sep. 9, 2008    (DE) .................. 10 2008 046 300

(51) Int. Cl.
A61B 18/16    (2006.01)
A61B 18/14    (2006.01)
A61B 18/00    (2006.01)

(52) U.S. Cl.
CPC .............. *A61B 18/16* (2013.01); *A61B 18/14* (2013.01); *A61B 2018/00589* (2013.01);
(Continued)

(58) Field of Classification Search
CPC ....... A61B 18/14; A61B 18/042; A61B 18/16; A61B 2010/1475; A61B 2010/00196;
(Continued)

(56) References Cited

U.S. PATENT DOCUMENTS 3,848,600 A  * 11/1974 Patrick, Jr. ............. A61B 18/16
                                                        606/32
4,343,308 A     8/1982 Gross
(Continued)

FOREIGN PATENT DOCUMENTS

DE        696 25 716 T2    4/2004
DE   10 2004 010 940 A1    9/2005
(Continued)

*Primary Examiner* — Michael F Peffley
*Assistant Examiner* — Samantha M Good
(74) *Attorney, Agent, or Firm* — Blank Rome LLP

(57) ABSTRACT

In surgery using monopolar HF, there is a constant risk of patients suffering burns at the neutral electrode. Said problem stems from the fact that numerous methods have been devised by which relatively high HF currents are applied for extended periods of time. The present invention solves said problem by providing a neutral electrode, device that is to be used for applying an HF current to a biological tissue. Said improved neutral electrode device comprises at least one latent heat accumulator for absorbing heat. Thus heat peaks can be at least temporarily accumulated until the accumulated thermal energy can be safely released.

9 Claims, 2 Drawing Sheets

(52) U.S. Cl.
CPC ............... *A61B 2018/00601* (2013.01); *A61B 2018/00607* (2013.01); *A61B 2018/00791* (2013.01)

(58) Field of Classification Search
CPC  A61B 2010/00583; A61B 2010/00589; A61B 2010/00601; A61B 2010/00607; A61B 2010/00791
See application file for complete search history.

(56) References Cited

U.S. PATENT DOCUMENTS

| | | |
|---|---|---|
| 4,387,714 A | 6/1983 | Geddes et al. |
| 6,241,723 B1 | 6/2001 | Heim et al. |
| 6,287,305 B1 | 9/2001 | Heim et al. |
| 8,021,360 B2 | 9/2011 | Dunning et al. |
| 8,231,614 B2 | 7/2012 | Dunning et al. |
| 2002/0128641 A1 | 9/2002 | Underwood et al. |
| 2002/0198523 A1 | 12/2002 | Behl |
| 2005/0154385 A1 | 7/2005 | Heim et al. |
| 2007/0005052 A1 | 1/2007 | Kampa |
| 2007/0005060 A1 | 1/2007 | Heim et al. |
| 2007/0049916 A1* | 3/2007 | Isaacson ................ A61B 18/16 606/32 |
| 2007/0123853 A1 | 5/2007 | Nesbitt |
| 2008/0097558 A1 | 4/2008 | Eggers et al. |
| 2008/0249521 A1* | 10/2008 | Dunning ................ A61B 18/16 606/35 |
| 2008/0281310 A1* | 11/2008 | Dunning ................ A61B 18/16 606/32 |
| 2009/0149930 A1 | 6/2009 | Schenck |
| 2009/0209953 A1 | 8/2009 | Schoenman |
| 2009/0254075 A1 | 10/2009 | Paz et al. |
| 2010/0185195 A1 | 7/2010 | McPherson |
| 2011/0166568 A1 | 7/2011 | Hagg et al. |
| 2011/0202055 A1 | 8/2011 | Selig |

FOREIGN PATENT DOCUMENTS

| | | |
|---|---|---|
| EP | 1 905 372 A1 | 4/2008 |
| EP | 1 905 374 A1 | 4/2008 |
| JP | 2004-508083 A | 3/2004 |
| WO | WO 02/19895 | 3/2002 |
| WO | WO 02/060526 A1 | 8/2002 |
| WO | WO 2007/013076 A2 | 2/2007 |
| WO | WO 2010/028750 | 3/2010 |

\* cited by examiner

NEUTRAL ELECTRODE DEVICE, ELECTROSURGICAL INSTRUMENT COMPRISING A CORRESPONDING NEUTRAL ELECTRODE DEVICE

CROSS-REFERENCE TO RELATED APPLICATIONS

This application is a divisional of U.S. patent application Ser. No. 13/062,755, filed on Mar. 8, 2011 and now abandoned, which is the U.S. national stage of International Application No. PCT/EP2009/006186, filed Aug. 26, 2009, the entire disclosures of which are incorporated by reference herein.

FIELD OF THE INVENTION

Embodiments of the invention relate to a neutral electrode device comprising a latent heat accumulator, an electrosurgical instrument with a corresponding electrode device, a contact medium with a latent heat accumulator and the use of a latent heat accumulator for cooling an electrode.

BACKGROUND

In high frequency surgery (HF surgery), alternating currents are passed through the human body at high frequency to damage or cut tissues in a targeted way. A substantial advantage over conventional scalpel cutting techniques is provided because suppression of bleeding can take place simultaneously with the incision by closing the relevant vessels.

A monopolar technique is often used. With such a technique, one pole of the HF voltage source is connected to the patient over the largest area possible. This electrode is known as the neutral electrode. The other pole (the active electrode) is situated on a surgical instrument. The current flows from the active electrode to the neutral electrode. The current density is highest in the immediate vicinity of the active electrode and this is where coagulating or parting of the tissue takes place.

When using neutral electrodes, one must ensure that the contact resistance between the skin and the contacting electrode is not too high. This would lead to severe heating of the biological tissue and occasionally to burns. Recently, the problem has presented itself that more methods have been developed by which relatively large HF currents are applied over longer periods of time. The risk of a burn at the neutral electrode is therefore increased. It should also be noted that, due to the physical conditions, the maximum heating occurs at the edge regions of the neutral electrode. The risk of burning is therefore particularly high in these edge regions.

Large area neutral electrodes are used to prevent unwanted damage to the tissue by contributing to reducing the current density in the immediate vicinity of the neutral electrode. Monitoring devices, which recognize partial detachment of the neutral electrode and react to this event accordingly, also exist.

Currently, applicable standards prescribe tests that limit a temperature rise at the neutral electrode, upon application of a particular current over a predetermined time period, to a maximum value.

With the solutions that are conventionally selected, a further problem exists wherein the area of the neutral electrode cannot be increased without restriction, otherwise the application would no longer be practical. Suitable placement of the neutral electrode becomes more difficult with its increasing size. Furthermore, in pediatric surgery, narrow limits apply to the size of the electrode.

The monitoring devices known and used today can only indirectly determine the degree of risk because it is usually only the electrical contact resistance between the neutral electrode and the patient that is measured, which only has a vague correlation to the application area.

As mentioned above, the current densities at the neutral electrode are not evenly distributed. For example, severe heating leading to burning can occur at the edges. Monitoring these local effects is extremely difficult.

SUMMARY

Based upon this prior art, it is an object of the embodiments disclosed herein to provide an improved neutral electrode device. In particular, damage to the tissue by the HF current in the region of the neutral electrode is to be prevented. Furthermore, a correspondingly improved electrosurgical instrument and contact medium are disclosed.

In particular, the object is achieved by a neutral electrode device for application of an HF current to a biological tissue, wherein the device comprises at least one latent heat accumulator for absorbing heat.

The core of the embodiments actively counteract burning because a temperature rise in a critical region is sufficiently prevented by cooling effects. The neutral electrode device according to the disclosed embodiments comprises a latent heat accumulator for this purpose, which absorbs the thermal peaks that occur during treatment and accumulates them over a long time period. It is therefore possible to absorb brief temperature rises. The accumulated thermal energy can be released during the operation or following the operation. Thus, a thermal safety reserve that effectively prevents critical temperature rises, even during relatively long activation cycles using large currents, can be built into the neutral electrode arrangement.

The neutral electrode device can comprise at least one electrode, particularly made from aluminum, wherein the latent heat accumulator is arranged flat on the electrode. It is advantageous for the latent heat accumulator to be distributed over the whole electrode surface to absorb heat energy. The heat energy can therefore always be absorbed where it arises. It is also possible for the latent heat accumulator to be distributed to conform to the distribution of heat where it arises. For example, a latent heat accumulator of large capacity could be provided at the edges of the electrode.

On application, the latent heat accumulator can be arranged on a side of the electrode facing away from the biological tissue. The latent heat accumulator therefore does not interfere with the application of the HF current. In particular, it does not act as a resistor, which can lead to an unwanted rise in the temperature of the neutral electrode device. Direct contact between the latent heat accumulator and the biological tissue is also prevented. Possible compatibility problems with the hydrogel used on application can also be prevented. Reliable uptake of the thermal energy can be achieved by direct contacting of the electrode.

The neutral electrode device can comprise at least one supporting fiber layer having phase change materials (PCMs). It is usual to apply the electrodes of the neutral electrode device to a flexible woven fabric or supporting non-woven fabric to enable optimal contact with the individual anatomical structures of the patient. The phase change material can complement or replace this supporting non-woven fabric. For example, PCM fibers can be worked into the supporting non-woven fabric. Alternatively, the supporting non-woven fabric can be replaced with PCM fibers.

Alternatively or additionally, the neutral electrode device can comprise a latent heat accumulator having a cooling cushion. The cooling cushion could be applied, for example, to the neutral electrode device. In this way, large quantities of the material of the latent heat accumulator could be made. A suitable cooling cushion could also be reused. Handling of the cooling cushion is very simple. The cushion can be exchanged during the operation. When overheating of the electrodes would occur during the operation, such that the capacity of the latent heat accumulator is used up, the exchange would be possible without any substantial difficulty.

The object of the disclosed embodiments is also achieved with an electrosurgical instrument for coagulating and/or cutting tissue, wherein the instrument comprises a neutral electrode device as described above. The same advantages result therefrom.

The object of the disclosed embodiments can also be solved with a contact medium for improving the electrical contact between an electrode and a biological tissue, wherein the contact medium comprises at least one latent heat accumulator for absorbing heat, and a conducting substance. It is therefore possible to provide a contact medium for neutral electrodes that improves the contact between the electrode and the biological tissue. The contact medium also comprises a latent heat accumulator, which is suitable for absorbing the arising heat. A particular advantage of the contact medium is that the latent heat accumulator can absorb the thermal energy of the electrode and the electrical tissue. No adaptation of the neutral electrode is necessary.

The conducting substance can come from the viscoelastic group of fluids. In particular, the conducting substance can be a hydrogel. Hydrogel is particularly well suited for improving the electrical contact between electrodes and biological tissue. Hydrogel can also be easily applied. Phase change material can also be mixed into the hydrogel, for example, in powder form. It is also possible to use a two-layered gel, where the lower layer that is in contact with the biological tissue is the conductive substance or the hydrogel and the upper layer is a phase change material in gel form.

The object of the disclosed embodiments is also achieved by the use of a latent heat accumulator for cooling a neutral electrode, particularly for HF surgical applications.

This also has similar advantages to those described above.

The above-described latent heat accumulator can be a phase change material, particularly from the paraffin group of materials.

For ease of processing, the phase change material can be encapsulated in silicate or synthetic fibers.

The latent heat accumulator can have a melting point that is lower than a maximum temperature at which thermal damage to biological tissue would occur. The latent heat accumulator is therefore only activated once the biological tissue or the neutral electrode device approaches a critical temperature. In this way, the resources of the latent heat accumulator can be optimally utilized.

The maximum temperature can be lower than 70° C., particularly lower than 60° C., 50° C., 40° C., 35° C., or 30° C.

Suitably, the melting point of the material used should be chosen so that it is higher than the surface temperature of the biological tissue. In particular, the melting point should be higher than a minimum temperature, particularly higher than 20° C., or 25° C.

BRIEF DESCRIPTION OF THE DRAWINGS

Embodiments of the invention will now be described in greater detail with reference to the drawings, in which.

DETAILED DESCRIPTION

In the description that follows, the same reference signs are used for the same and similarly acting parts.

Figure 1:
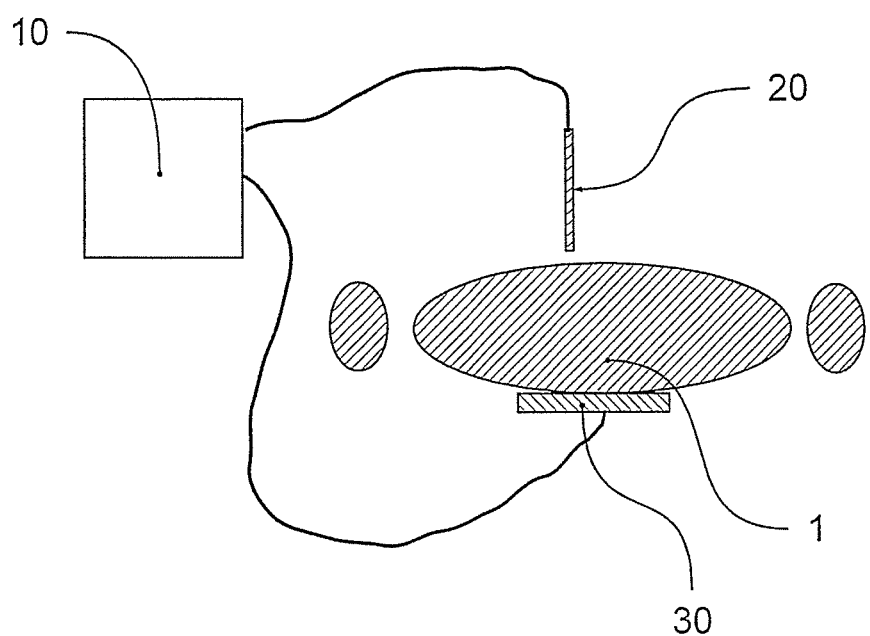
FIG. 1 illustrates a monopolar electrosurgical instrument for coagulating and/or cutting tissue.

FIG. 1 shows an electrosurgical device comprising an HF generator 10, a monopolar instrument 20 and a neutral electrode arrangement 30. On application of HF current, a voltage is applied between the monopolar instrument 20 and the neutral electrode 30. The HF treatment current flows through the body being treated, a torso 1 in the illustrated embodiment. The current density in the immediate vicinity of the monopolar instrument 20 is high such that the tissue being contacted is coagulated or parted.

To avoid burning at the neutral electrode 30, according to the illustrated embodiment, a latent heat accumulator should be provided. As shown in FIGS. 2-5, neutral electrode arrangement 30 usually comprises three layers. Adjacent to the biological tissue is the electrode layer, comprising a plurality of mutually electrically separated electrodes 34, 34'. A PET support 33, which is glued to a supporting non-woven fabric 32, is provided on the electrodes 34, 34'.

A hydrogel 36 (or 36') is applied to improve the electrical contact between the biological tissue and the electrodes 34, 34'.

Figure 2:
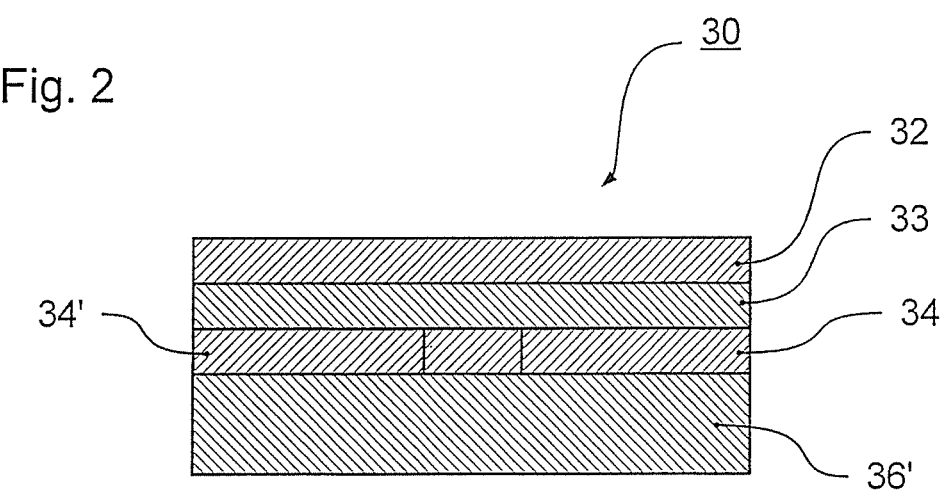
FIG. 2 illustrates a neutral electrode comprising hydrogel, wherein PCM is added to the hydrogel.

In the first exemplary embodiment (see FIG. 2), the latent heat accumulator is contained in the hydrogel 36. FIG. 2 shows a hydrogel 36' with PCM components. The PCM is in powder form and is mixed into the hydrogel 36.

Figure 3:
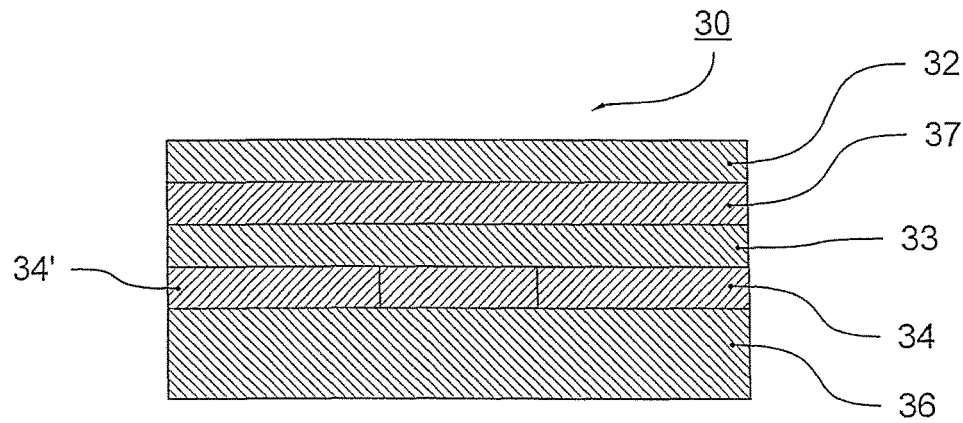
FIG. 3 illustrates a neutral electrode with an additional PCM layer.
Figure 4:
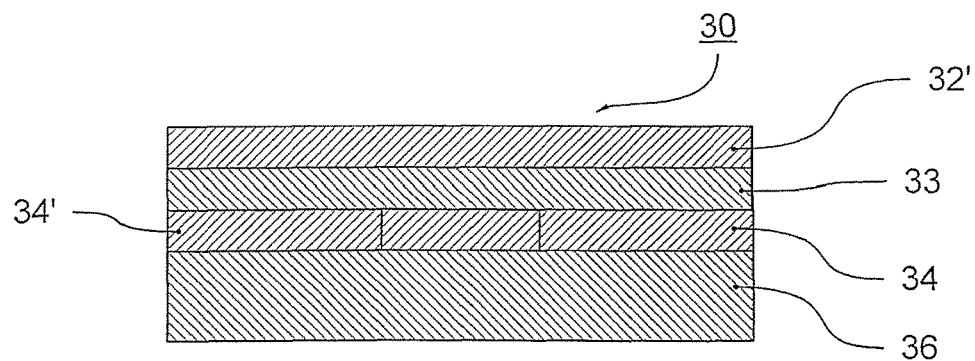
FIG. 4 illustrates a neutral electrode with a supporting non-woven fabric made from PCM fibres.
Figure 5:
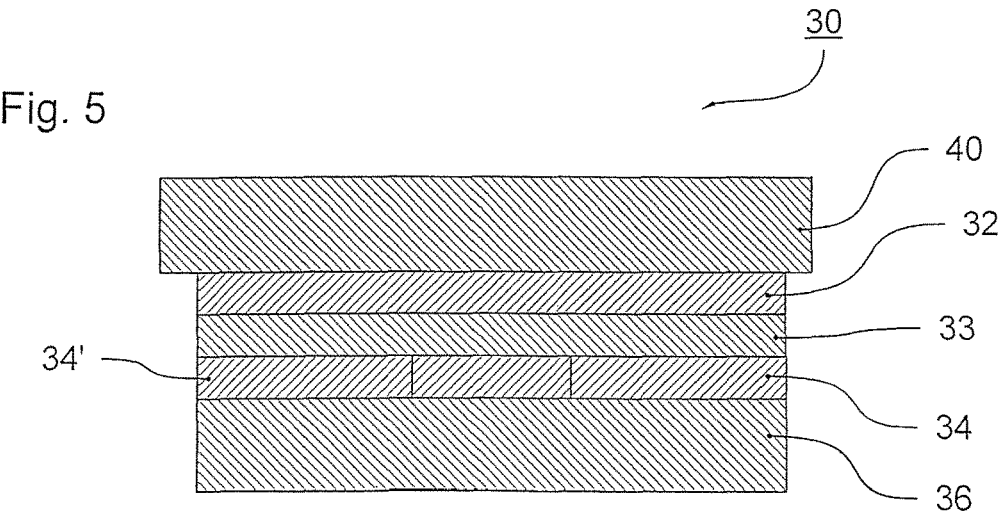
FIG. 5 illustrates a neutral electrode with a PCM cushion.

In a second exemplary embodiment, shown in FIG. 3, the neutral electrode arrangement 30 has an additional PCM layer 37 arranged between the supporting non-woven fabric 32 and the PET support 33. It is also possible to use a metal alloy with a low melting point. A thermally conductive contact to the electrodes 34, 34' can be made via the PET support 33. The heat arising at the electrodes 34, 34' can therefore be absorbed by the PCM layer 37. Alternatively, the PET support 33 can be dispensed with or replaced with PCM.

In a third exemplary embodiment (see FIG. 4), the neutral electrode arrangement 30 has an adapted supporting non-woven fabric. This is a supporting non-woven fabric 32' with PCM fibres. These fibres are known in the textile industry and can readily be processed into a woven fabric structure. Direct contacting of the biological tissue with the PCM is prevented by use of the supporting non-woven fabric 32' with PCM fibres. Low demands can therefore be placed on the tolerability of the PCM used.

In a fourth exemplary embodiment (see FIG. 5), the neutral electrode arrangement 30 is complemented with a PCM cushion 40. The cushion 40 can be applied over a large area on the neutral electrode arrangement 30 after placement of the neutral electrode arrangement 30 on the biological tissue and can serve as the latent heat accumulator.

The cushion 40 is very easy to use and large amounts of the phase change material can be arranged therein. The PCM cushion 40 therefore has a large storage capacity.

Some concrete exemplary embodiments of the use of PCM in conjunction with the neutral electrode arrangement 30 have been described. However, it is also possible to combine the individual exemplary embodiments with one another. For example, the hydrogel 36' with PCM components can be used in conjunction with the PCM cushion 40.

The invention claimed is:

1. A neutral electrode device for application of an HF current to a biological tissue, comprising:
    at least one electrode having a first side and a second side, the first side away from the biological tissue and the second side configured to be next to the biological tissue;
    at least one supporting fiber layer with non-woven fabric, the at least one supporting fiber layer having phase change materials (PCM) and being distributed over the whole first side of the at least one electrode, the phase change materials complementing the non-woven fabric, absorbing heat and functioning as a latent heat accumulator; and
    hydrogel on the second side of the at least one electrode,
    wherein the at least one electrode is applied to the at least one supporting fiber layer and the phase change materials are arranged on the first side of the at least one electrode,
    wherein the phase change materials have a melting point lower than a maximum temperature at which thermal damage to the biological tissue occurs, wherein the maximum temperature is lower than 70° C., and
    the phase change materials absorbing heat by melting as the temperature approaches the maximum temperature.

2. The neutral electrode device of claim 1, further comprising a PET support on the electrode which is glued to the non-woven fabric, wherein the PET support makes a thermal conductive contact between the phase change materials and the electrode.

3. The neutral electrode device of claim 1, wherein the electrode is made from aluminum.

4. The neutral electrode device of claim 1, wherein the phase change materials are selected from the paraffin group of materials.

5. The neutral electrode device of claim 1, wherein the phase change materials are encapsulated in silicate or synthetic fibers.

6. The neutral electrode device of claim 1, wherein the maximum temperature is lower than 50° C.

7. The neutral electrode device of claim 1, wherein the melting point is higher than a minimum temperature, namely higher than 25° C.

8. The neutral electrode device of claim 1, wherein the neutral electrode device is part of an electrosurgical instrument for coagulating and/or cutting tissue.

9. A neutral electrode device for application of an HF current to a biological tissue, the neutral electrode device comprising:
    at least one latent heat accumulator for absorbing heat;
    at least one electrode having a first side and a second side, the first side configured to face away from the biological tissue and the second side configured to be next to the biological tissue, wherein the at least one latent heat accumulator is distributed over the whole first side of the at least one electrode to absorb heat energy, wherein the latent heat accumulator comprises at least one supporting fiber layer with non-woven fabric, the at least one supporting fiber layer having a phase change material from the paraffin group of material; and
    hydrogel on a second side of the at least one electrode,
    wherein the latent heat accumulator is arranged on the first side of the at least one electrode, wherein the melting point of the latent heat accumulator is higher than 25° C. and lower than 50° C.

* * * * *